United States Patent [19]

Yang et al.

[11] Patent Number: 4,970,164

[45] Date of Patent: Nov. 13, 1990

[54] METHODS OF RECOVERING AND SEPARATING WATER-SOLUBLE CYCLODEXTRINS FROM CYCLODEXTRIN FORMATION LIQUID

[75] Inventors: Chin-Ping Yang; Chein-Shyong Su, both of Taipei, Taiwan

[73] Assignee: Tatung Co., Taipei, Taiwan

[21] Appl. No.: 334,199

[22] Filed: Apr. 6, 1989

[51] Int. Cl.$^5$ .................. C08B 37/16; C12P 19/04; C12P 19/18

[52] U.S. Cl. .................. 435/280; 435/95; 435/96; 435/97; 435/101; 536/103

[58] Field of Search .............. 536/103; 435/95, 96, 435/101, 280, 97

[56] References Cited

U.S. PATENT DOCUMENTS 3,541,077  11/1970  Armbruster .................. 536/103
4,738,923  4/1988   Ammeraal .................... 536/103
4,808,232  2/1989   Beesley ....................... 536/103
4,835,105  5/1989   Sergs et al. .................... 435/97
4,840,679  6/1989   Ammeraal et al. ............ 536/103
4,904,307  2/1990   Ammeraal et al. ............ 536/103

*Primary Examiner*—Herbert J. Lilling
*Attorney, Agent, or Firm*—Brumbaugh, Graves, Donohue & Raymond

[57] ABSTRACT

A method of recovering and separating water-soluble cyclodextrins from cyclodextrin formation liquid, wherein the CD formation liquid or the CD liquid after separating β-CD by concentrated precipitation method is mixed with α-amylase to hydrolyze dextrins to small oligosaccharides, then is concentrated and precipitated again to separate the remained β-CD, after that, soluble α- and γ-CD are recovered by using inclusion extraction method with organic solvent from the residual liquid.

4 Claims, No Drawings

METHODS OF RECOVERING AND SEPARATING WATER-SOLUBLE CYCLODEXTRINS FROM CYCLODEXTRIN FORMATION LIQUID

BACKGROUND OF THIS INVENTION

This invention relates to a method which can recover expensive soluble cyclodextrin from CD formation liquid.

Solutions containing cyclodextrins (CDs) and linear dextrins produced during the reaction of starch with CGTase are called CD formation liquid. CD formation liquids include $\alpha$-, $\beta$-and $\gamma$-CD.

$\alpha$-CDs and $\gamma$-CD's are water-soluble. Unfortunately, the soluble CDs have not been recovered from CD formation liquid after separating $\beta$-CD and have instead been used as food additives with dextrins after being concentrated to syrup.

Since Horikoshi found that a cyclodextrin glycosyltransferase (CGTase) isolated from alkalophilic Bacillus is suitable for producing cyclodextrin (CD), this enzyme has been used to produce $\beta$-cyclodextrin ($\beta$-CD) in industrial scale. In this method starch is suspended in water solution and hydrolyzed to soluble starch at elevated temperature (80°-85° C.) by CGTase (using CGTase as amylase could reduce the formation of glucose which would inhibit the formation of CD at next process), then the soluble starch is mixed with CGTase again at about 50°-60° C. to obtain CD. The conversion from starch to CD is related to the concentration of substrate (soluble starch) and reaction conditions. 25-32% conversion is obtained at 15% (w/v) of reaction substrate and the conversion is increased to 50% at 5% of substrate residual starch becomes linear dextrins. The contents of the produced CD vary with the type of the CGTase and the reaction conditions, about 4.3%, 77% and 20% of $\alpha$-, $\beta$- and $\gamma$-CD respectively are obtained from 5% of starch by using CGTase from Bacillus sp. No. 38-2. The CD formation liquid is decolorized by active carbon, de-ionized by ion-exchange resin, and concentrated by evaporation. Then $\beta$-CD (with lower solubility) is precipitated after being cooled to room temperature. The soluble $\alpha$-, $\gamma$-CD and a little residual $\beta$-CD are not separated and recovered and thus stay with dextrins as syrup liquid or are dried to powder and cheaply used as food filler and additives. The wholesale price of $\beta$-CD in the international market is already diminished to U.S. $12/kg due to its easy production. But the international price of soluble CD such as $\gamma$-CD is still about U.S. $1200/kg because of production difficulties and it's about 100 times to that of $\beta$-CD.

SUMMARY OF THE INVENTION

In accordance with the present invention, water-soluble cyclodextrins can be separated from cyclodextrin formation liquid by a process comprising the steps of (a) separating substantially all of the $\beta$-cyclodextrin from the cyclodextrin formation liquid to produce a residual liquid containing the water-soluble cyclodextrins and linear dextrins; (b) adding an amylase enzyme that hydrolyzes linear dextrins without degrading cyclodextrins to either the cyclodextrin formation liquid or the residual liquid whereby the linear dextrins are hydrolyzed to yield a low viscosity residual liquid; and (c) extracting the water-soluble cyclodextrins from the low viscosity residual liquid using an organic solvent. Suitable enzymes for use in hydrolyzing the linear dextrins include $\alpha$-amylase and glucoamylase.

DETAILED DESCRIPTION OF THE INVENTION

Based on the conditions of CD production described above, this invention could recover the valuable CD ($\alpha$- and $\gamma$-CD) from CD formation liquid or the solution (called syrup after being concentrated) after separating $\beta$-CD. The method is to add enzyme in CD formation liquid to hydrolyze the linear dextrin to small saccharides or glucose to reduce the viscosity, $\beta$-CD (with lower solubility) may be crystallized and separated after concentration. Then organic solvent which has low boiling temperature and the ability to form inclusion compound with CD is used to extract or precipitate the soluble CD. This invention describes the method of separating and recovering the soluble CD.

There are two main subjects in this method, first is the separation of $\beta$-CD by concentrated crystallization method according to the solubility differences between CDs, then soluble CD ($\gamma$-CD etc.) is extracted using organic solvent entrapment method. According to the same principle, all CD could be extracted first by solvent then $\beta$-CD is separated from other CD by its lower solubility and the residual soluble CD is recovered by solvent entrapment method again. Second is the reduction of interference of viscous dextrin during the separation operation. In order to reduce the difficulty probably arising during the above operation, in this invention the dextrins in CD formation liquid are hydrolyzed to small saccharides or glucose as possible, or even converted to ethanol. But the enzyme used in hydrolyzing dextrins should be selected to reserve CD such as $\alpha$-amylase from Bacillus subtilis and glucoamylase from Rhizopus niveus.

The organic solvent used in extracting CD should be able to form inclusion compound with CD, insoluble with water, low boiling point and volatile such as trichloroethylene, dichloromethane, chloroform and acetone etc.

EXAMPLE 1

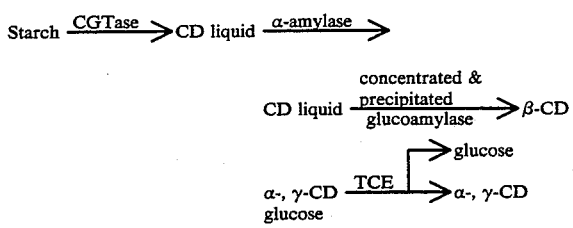

200 mL (5% wt, containing 10 g starch) of starch solution is stirred and heated to 60° C., then 32 mg of CGTase is added and increase the temperature to 85° C. for 30 min of reaction. After cooling to room temperature, 50 mg of CGTase is added and stirred for 23 h at 55° C. The reaction is stopped by heating the mixture at 100° C. for 10 min to inactivate the enzyme, then 0.6 mL of $\alpha$-amylase (Novo BAN-240L) is added and stirred at 85°-90° C. for 10 min. The mixture is concentrated to 20 mL and white crystal is obtained after cooling to room temperature, 3.43 g of $\beta$-CD is achieved after filtration and dried. The residual liquid (can be concentrated to syrup) is filled to 100 ml with water and adjusted to pH 5.0, 8 mg of glucoamylase is added and reacted at 40° C.

for 24 h. After cooling to room temperature 60 ml of TCE is added and stirred thoroughly, white precipitate is formed and collected by centrifuge and filtration. After dried in oven, 1.06 g of white solid is obtained (which contains 0.05 g α-CD, 0.15 g β-CD, 0.83 g γ-CD), 98% purity of CD. The remaining filtrate is dried to give 5.57 g solid (contains 0.14 g α-CD, 0.05 g β-CD, 0.07 g γ-CD and 5.2 g of glucose), 93.4% purity of glucose.

EXAMPLE 2

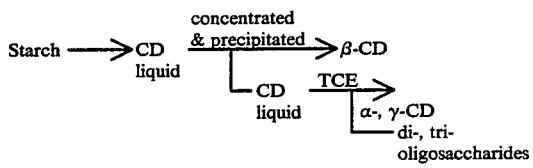

CD liquid is prepared as the methods described in example 1. During the hydrolysis of dextrin by α-amylase, an enzyme which wouldn't decompose CD is selected and the hydrolysis time is increased in order to completely hydrolyze dextrin to smaller oligosaccharides. The reaction mixture is concentrated to about 20 ml and white crystalline is obtained after cooled, it is filtered and dried to give 3.04 g of β-CD. The remaining liquid is filled to 100 ml with water and stirred with 60 ml of TCE thoroughly to form white precipitate, 1.04 g of white solid (contains 0.83 g γ-CD, 0.05 g α-CD, 0.14 g β-CD) is achieved after centrifuge, filtration and dried in oven. The final residual liquid could be hydrolyzed to glucose by adding glucoamylase.

EXAMPLE 3

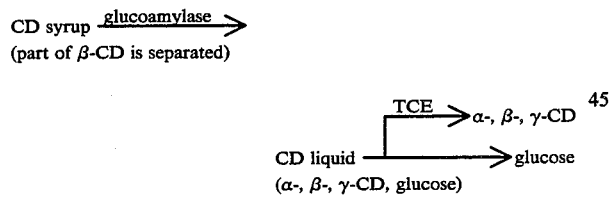

20 g of CD syrup (prepared from 15 wt % starch) which contains 11.7 g of sugar content and 0.23 g, 0.637 g, 1.18 g of α-, β-, and γ-CD is dissolved in water to 400 ml of total volume and adjusted to pH 5.0 by HCl, then 16 mg of glucoamylase is added to react at 40° C. for 24 h. After cooled to room temperature 240 ml of TCE is added and stirred thoroughly to form white precipitate, 1.60 g of white solid (contains 1.036 g γ-CD and 0.01 g, 0.51 g of α- and β-CD) is obtained after filtration and dried in oven. The soluble CD in solid is dissolved by 10 ml of cold distilled water, the residue is 0.33 g of β-CD and the filtrate is dried to give 1.216 g of solid (contains 1.036 g γ-CD, 0.18 g β-CD, and 0.01 g of α-CD). The initial filtrate (from first filtration) is dried to give 11.8 g of solid (contains 0.054 g, 0.016 g, 0.023 g α-, β-, γ-CD and 11.23 g glucose)

EXAMPLE 4

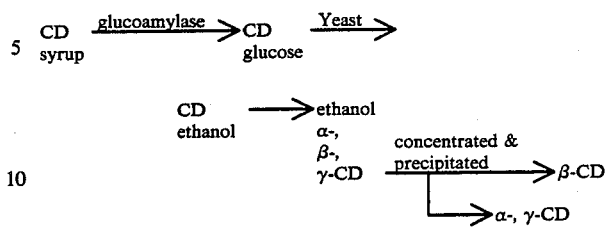

150 ml of CD liquid (contains 4.28 g sugar, 0.086 g, 0.239 g, and 0.443 g of α-, β-, and γ-CD) is mixed with 5 mg of glucoamylase at pH 5.0 and 40° C. for 24 h, then 3.1 g of yeast is added to react at pH 5.0 and 35° C. for 48 h. The reaction mixture is then filtered and de-colored by active carbon, the supernatent is collected and mixed with TCE to form precipitate. 0.635 g of white solid (contains 0.069 g, 0.226 g, and 0.390 g of α-, β-, and γ-CD), the recovery percentage of α-, β-, and γ-CD is 80, 95, 88% respectively.

EXAMPLE 5

100 ml of CD liquid (contains sugar 11.4 g and 0.23 g, 0.637 g, and 1.18 g of α-, β-, and γ-CD) is mixed and stirred with 60 ml of TCE to give white precipitate, the precipitate is collected by centrifuge then mixed with 50 ml of water and 30 ml of TCE and repeat the TCE precipitation again. Finally the white precipitate is filtered and dried to give 1.914 g of solid (contains β- and γ-CD 0.620 g and 1.115 g), the purity of CD is 91%, the recovery percentage of β- and γ-CD is 97.4 and 94.5% respectively. This white solid is dissolved, filtered, and concentrated again to separate 0.37 g of β-CD and a powder contains 1.014 g γ-CD and 0.19 g β-CD.

What is claimed is:

1. A method of recovering and separating water-soluble cyclodextrins from cyclodextrin formation liquid containing β-cyclodextrin and water-soluble cyclodextrins, which comprises
   (a) separating substantially all of the β-cyclodextrin from the cyclodextrin formation liquid to produce a residual liquid containing the water-soluble cyclodextrins and linear dextrins;
   (b) adding an amylase enzyme that hydrolyzes linear dextrins without degrading cyclodextrins to either the cyclodextrin formation liquid or the residual liquid whereby the linear dextrins are hydrolyzed to yield a low viscosity residual liquid; and
   (c) extracting the water-soluble cyclodextrins from the low viscosity residual liquid using an organic solvent.

2. The method according to claim 1, wherein the β-cyclodextrins are separated from the cyclodextrin formation liquid by the steps of concentrating the cyclodextrin formation liquid, precipitating the β-cyclodextrin, and removing the precipitate from the cyclodextrin formation liquid.

3. The method according to claim 1, wherein the enzyme is selected from the group consisting of α-amylase and glucoamylase.

4. The method according to claim 1, wherein the organic solvent is selected from the group consisting of trichloroethylene, dichloroethylene, chloroform and acetone.

* * * * *